United States Patent [19]

Savides et al.

[11] Patent Number: 4,537,993

[45] Date of Patent: Aug. 27, 1985

[54] BIS(β-CARBOXYETHYL)ISOBUTYL, SEC. BUTYL AND T-BUTYL PHOSPHINE OXIDE AND POLYAMIDES CONTAINING THE SAME

[75] Inventors: Christos Savides, Fairfield, Conn.; Allan J. Robertson, Thorold, Canada

[73] Assignee: American Cyanamid Company, Stamford, Conn.

[21] Appl. No.: 621,760

[22] Filed: Jun. 18, 1984

Related U.S. Application Data

[63] Continuation-in-part of Ser. No. 591,287, Mar. 19, 1984, abandoned.

[51] Int. Cl.³ ............................................. C07F 9/53
[52] U.S. Cl. ................................. 568/14; 528/337; 528/310
[58] Field of Search ........................................... 568/14

[56] References Cited

U.S. PATENT DOCUMENTS

| | | | |
|---|---|---|---|
| 3,657,352 | 4/1972 | Kleiner | 568/14 |
| 4,315,867 | 2/1982 | Hänssle | 568/14 X |
| 4,328,163 | 5/1982 | Hänssle | 568/14 X |
| 4,346,236 | 8/1982 | Lee | 568/14 X |
| 4,474,675 | 10/1984 | Cummins et al. | 568/14 X |

OTHER PUBLICATIONS

Chemical Abstracts 88, 152776n, (1978).
Kosolapoff et al., Organic Phosphorus Compounds, Wiley-Interscience N.Y., vol. 1, pp. 61–68, vol. 3, pp. 343–349, (1972).
Fieser and Fieser, Basic Organic Chemistry, D. C. Heath & Co., Boston, p. 36, (1959).

*Primary Examiner*—Helen M. S. Sneed
*Attorney, Agent, or Firm*—Frank M. Van Riet

[57] ABSTRACT

The compounds bis (β-carboxyethyl)isobutyl phosphine oxide, bis (β-carboxyethyl) sec. butyl phosphine oxide and bis(β-carboxyethyl)-t-butyl phosphine oxide and their use as components in the production of fiber-forming polyamides, fibers produced from said polyamides and a method for the production of various bis (carboxyalkyl) alkyl phosphine oxides are disclosed.

4 Claims, No Drawings

BIS(β-CARBOXYETHYL)ISOBUTYL, SEC. BUTYL AND T-BUTYL PHOSPHINE OXIDE AND POLYAMIDES CONTAINING THE SAME

CROSS-REFERENCE TO RELATED APPLICATIONS

This application is a continuation-in-part of our co-pending application, Ser. No. 591,287, filed Mar. 19, 1984, now abandoned.

BACKGROUND OF THE INVENTION

U.S. Pat. Nos. 4,032,517 and 4,092,302 are directed to fiber-forming polyamides containing phosphorus wherein the phosphorus is present as radicals of the formula:

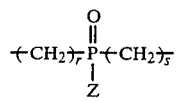

wherein Z is an alkyl radical having 1-4 carbon atoms and r and s are individually the integers 2 or 3. Fibers produced from these polyamides are disclosed as exhibiting permanent antistatic, moisture transport and flame-resistant properties. The only compounds specifically disclosed and exemplified in the above patent, however, are the methyl and ethyl derivatives, i.e. those derivatives wherein Z is methyl or ethyl.

SUMMARY OF THE INVENTION

It has now been found that when copolyamides are produced from the compound bis(β-carboxyethyl)isobutyl phosphine oxide, the compound bis(β-carboxyethyl)sec. butyl phosphine oxide or the compound bis(β-carboxyethyl)-t-butyl phosphine oxide, fibers produced therefrom exhibit less hygroscopicity and more flexibility than when the monoalkyl radical of the phosphine oxide is a methyl or ethyl radical, i.e. than when Z, above, is methyl or ethyl.

It has also been found that various bis(carboxyethyl)alkyl phosphine oxides can be produced more cheaply and with less contaminating salts present therein when the novel process described hereinbelow is employed in their production.

DESCRIPTION OF THE INVENTION INCLUDING PREFERRED EMBODIMENTS

The instant invention is directed to a compound having the formula

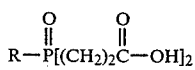

wherein R is a sec. butyl, an isobutyl or a t-butyl radical.

The instant invention also relates to fiber forming copolyamides consisting essentially of the recurring units

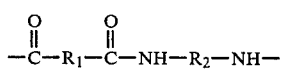

and

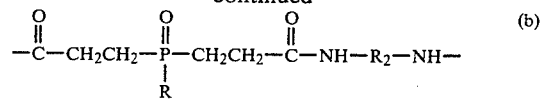

wherein R is as described above and $R_1$ and $R_2$, individually, are selected from the group consisting of polymethylene of 4-12 carbon atoms, inclusive, m-phenylene and p-phenylene, wherein the copolyamide contains a sufficient amount of unit (b) to provide from about 0.5% to about 7.0%, by weight, of phosphorus thereto.

Furthermore, this invention relates to a process for the production of a compound having the formula:

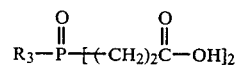

wherein $R_3$ is an alkyl radical having from 2-6 carbon atoms, inclusive, which process is enumerated by the following, wherein $R_4$ is an alkyl radical of 1-4 carbon atoms, inclusive.

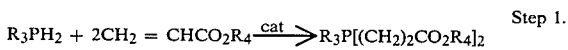 Step 1.

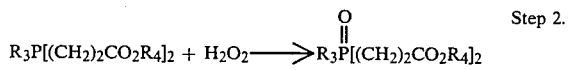 Step 2.

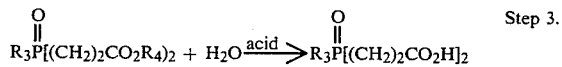 Step 3.

Step 1 is carried out in the presence of a free-radical generating catalyst such as azobisisobutyronitrile, the acrylate ester being used as a solvent solution in, for example, inert hydrocarbon solvents such as toluene, heptane, etc. at a temperature ranging from about 50° C. to about 110° C., preferably from about 70° C. to about 95° C.

Step 2, oxidation, is conducted at a temperature ranging from about 50° C. to about 80° C., preferably, from about 60° C. to about 70° C., utilizing a dilute (e.g. 10-40%) aqueous solution of an oxidizing agent such as hydrogen peroxide. Reaction is complete in from 1-5 hours. The resulting phosphine oxide is recovered as an oil by distillation of the solvent and water from the mixture.

Step 3 comprises hydrolysis of the phosphine oxide from Step 2 by utilization of a very dilute (i.e. 1-10%) aqueous acid solution. Sulfuric acid, hydrochloric acid, etc. may be used. The hydrolysis is conducted at reflux over a period of 5-10 hours, preferably 6-8 hours. Upon cooling, the desired product is recovered as a crystalline solid. Purification may be accomplished by recrystallization from water.

The copolyamides of this invention may be prepared by the condensation of difunctional polyamide-forming reactants, i.e. diamines and dicarboxylic acids etc. as disclosed in the above-cited patents, which patents are hereby incorporated herein by reference.

In general, unit (a) above is formed by the condensing of a dicarboxylic acid having the formula:

wherein n is an integer of 4–12, inclusive, with a diamine having the formula:

$$H_2N(CH_2)_nNH_2$$

wherein n is as defined above, unit (b) being present during said condensation reaction and being present in such quantities so as to result in the formation of a copolyamide having from about 0.5% to about 7.0%, by weight, of phosphorus in the copolyamide polymer chain.

The copolyamides of the present invention provide fibers with improved processing properties, mechanical properties (i.e. elongation, modulus of elasticity, etc.) and are less hydroscopic than fibers prepared from the methyl and ethyl bis(carboxyethyl)phosphine oxides as one of the components thereof.

The following examples are set forth for purposes of illustration only and are not meant to be construed as limitations on the present invention except as set forth in the appended claims. All parts and percentages are by weight unless otherwise specified.

EXAMPLE 1

Isobutylbis($\beta$-Carboxyethyl)Phosphine Oxide

A solution of 688 parts of methylacrylate in 285 parts of toluene is reacted with 450 parts of 80% isobutylphosphine in the presence of 3.9 parts of (azobisisobutyronitrile) initiator at 74°–93° C. for 7 hours. The resulting isobutylbis(carbomethoxyethyl)phosphine is oxidized with 600 parts of (10% excess) of 25% aqueous hydrogen peroxide. The reaction is complete within 2–3 hours at 65° C. and the resultant phosphine oxide is isolated as an oil following distillation of toluene and water from the mixture. The recovered phosphine oxide is hydrolyzed in 4 liters of 5% aqueous sulfuric acid solution by refluxing over a 7 hour period. On cooling, the product, isobutyl bis($\beta$-carboxyethyl)phosphine oxide is isolated as a white crystalline solid in 70% yield and purified by recrystallization from water, m.p. 186°–187° C.

EXAMPLE 2

Sec.Butyl Bis($\beta$-Carboxyethyl)Phosphine Oxide

Sec. butylphosphine, 592 parts (85% purity) is reacted with 860 parts of methyl acrylate containing 4.9 parts of azobis(isovaleronitrile) at 67°–100° C. for 3.5 hours. The reaction product, sec. butylbis(carbomethoxyethyl)phosphine is reacted with 10% molar excess hydrogen peroxide (25% solution) for two hours at 60° C. to give the corresponding phosphine oxide. The latter is hydrolyzed with dilute sulfuric acid to give after recrystallization from water, sec. butyl bis($\beta$-carboxyethyl)phosphine oxide.

EXAMPLE 3

T-Butyl Bis($\beta$-Carboxyethyl)Phosphine Oxide

The procedure of Example 1 is again followed except that 860 parts of methyl acrylate are reacted with 452 parts of t-butylphosphine. 4.9 Parts of azobis-1-isovaleronitrile are used as catalyst. The liquid reaction product, t-butyl bis(carbomethoxyethyl)phosphine is oxidized to give t-butyl bis(carbomethoxyethyl)phosphine oxide which is then hydrolyzed. The product, t-butyl bis($\beta$-carboxyethyl)phosphine oxide is isolated as an off-white crystalline solid having a m.p. of 174° C.

EXAMPLE 4

Using the procedure of Example 1, isopentyl phosphine is reacted at 70°–90° C. with ethylacrylate to give isopentylbis(carbethoxyethyl)phosphine. The latter is oxidized with hydrogen peroxide and hydrolyzed with aqueous dilute hydrochloric acid to give the corresponding acid, isopentylbis($\beta$-carboxyethyl)phosphine oxide.

EXAMPLE 5

Using a procedure similar to Example 1, hexylbis($\beta$-carboxyethyl)phosphine is prepared from hexyl phosphine and butylacrylate to give the phosphine, followed by oxidation and acid catalyzed hydrolysis to give the desired product.

EXAMPLE 6

A mixture of 180 parts of adipic acid hexamethylene diamine salt and 62.3 parts of bis($\beta$-carboxyethyl)isobutyl phosphine oxide is copolymerized in an autoclave at 200-250 psi under a nitrogen atmosphere at 200°–250° C. The water condensate is removed and the polymer melt is extruded through a multi-hole spinneret into a yarn which is drawn into a fiber. The yarn contains recurring units of the formula:

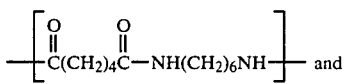 and

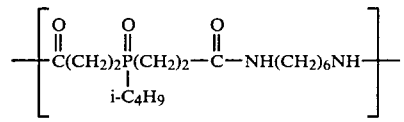

The fiber is not hygroscopic and exhibits excellent flexibility.

EXAMPLE 7

Following the procedure of Example 6, a polyamide fiber is prepared by the copolymerization of 180 parts adipic acid hexamethylene diamine salt and 68 parts of bis($\beta$-carboxyethyl)sec. butylphosphine oxide. The fiber exhibits essentially the same properties of that of Example 6.

EXAMPLE 8

Again following the procedure of Example 6, a polyamide fiber is prepared which contains recurring units produced from bis($\beta$-carboxyethyl)-t-butylphosphine oxide. Again the fiber shows enhanced flexibility and is not hygroscopic.

I claim:

1. A compound having the formula:

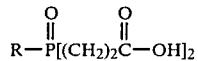

wherein R is a secondary butyl radical, an isobutyl radical or a t-butyl radical.

2. A compound according to claim 1 wherein R is a secondary butyl radical.

3. A compound according to claim 1 wherein R is an isobutyl radical.

4. A compound according to claim 1 wherein R is a t-butyl radical.

* * * * *